United States Patent
Minor et al.

(10) Patent No.: US 7,531,496 B2
(45) Date of Patent: May 12, 2009

(54) AZEOTROPE-LIKE COMPOSITIONS OF 1,1,1,3,3-PENTAFLUOROBUTANE

(75) Inventors: Barbara Haviland Minor, Elkton, MD (US); Melodie A. Schweitzer, Wilmington, DE (US); Thomas L. Tattersall, Wilmington, DE (US)

(73) Assignee: EI and Micro Care Corp, Bristol, CT (US)

( * ) Notice: Subject to any disclaimer, the term of this patent is extended or adjusted under 35 U.S.C. 154(b) by 484 days.

(21) Appl. No.: 11/169,344

(22) Filed: Jun. 29, 2005

(65) Prior Publication Data

US 2005/0267006 A1 Dec. 1, 2005

Related U.S. Application Data

(63) Continuation of application No. 09/528,962, filed on Mar. 21, 2000, now Pat. No. 6,951,835.

(60) Provisional application No. 60/125,511, filed on Mar. 22, 1999.

(51) Int. Cl.
*C11D 7/50* (2006.01)

(52) U.S. Cl. .................. 510/411; 510/408; 510/410; 510/412

(58) Field of Classification Search .................. 510/408, 510/410, 411, 412
See application file for complete search history.

(56) References Cited

U.S. PATENT DOCUMENTS

| 5,064,560 | A | 11/1991 | Merchant | 252/171 |
| 5,196,137 | A | 3/1993 | Merchant | 252/172 |
| 5,268,120 | A | 12/1993 | Michaud | 252/162 |
| 5,268,121 | A | 12/1993 | Michaud | 252/171 |
| 5,445,757 | A | 8/1995 | Pennetreau | 252/171 |
| 5,478,492 | A | 12/1995 | Barthelemy et al. | 252/171 |
| 6,951,835 | B1 * | 10/2005 | Minor et al. | 510/410 |

FOREIGN PATENT DOCUMENTS

| EP | 0 851 016 A1 | 12/1997 |
| EP | 0 856 578 A1 | 8/1998 |
| EP | 0 894 851 A1 | 2/1999 |
| EP | 0 974 642 A1 | 1/2000 |
| JP | 93168805 | 7/1993 |
| JP | 93171185 | 7/1993 |
| JP | 93171190 | 7/1993 |
| JP | 93302098 | 11/1993 |
| JP | 98036894 | 2/1998 |
| WO | WO 96/30487 | 10/1996 |
| WO | WO 96 36689 | 11/1996 |
| WO | WO 97/41189 | 11/1997 |
| WO | WO 98/50517 | 11/1998 |
| WO | WO 99/02616 | 1/1999 |
| WO | WO 99/31214 | 6/1999 |
| WO | WO 00/36046 | 6/2000 |

OTHER PUBLICATIONS

International Search Report, date of mailing: Jan. 29, 2001.

* cited by examiner

*Primary Examiner*—Gregory E Webb

(57) ABSTRACT

Disclosed are binary azeotrope-like compositions consisting essentially of 1,1,1,3,3-pentafluorobutane (HFC-365mfc) and 1,1,1,2,3,4,4,5,5,5-decafluoropentane (HFC-43-10mee) or nonafluoromethoxybutane. The present invention further includes ternary or quaternary azeotrope-like compositions consisting essentially of 1,1,1,3,3-pentafluorobutane and 1,1,1,2,3,4,4,5,5,5-decafluoropentane or nonafluoromethoxybutane, and additionally trans-1,2-dichloroethylene, n-propyl bromide, acetone, methanol, ethanol or isopropanol.

4 Claims, No Drawings

AZEOTROPE-LIKE COMPOSITIONS OF 1,1,1,3,3-PENTAFLUOROBUTANE

CROSS REFERENCE TO RELATED APPLICATIONS

This application is a continuation of allowed U.S. application Ser. No. 09/528,962, dated Mar. 21, 2000, which claims the priority benefit of U.S. provisional application 60/125,511, filed Mar. 22, 1999.

FIELD OF THE INVENTION

The present invention relates to binary azeotrope-like compositions consisting essentially of 1,1,1,3,3-pentafluorobutane and 1,1,1,2,3,4,4,5,5,5-decafluoropentane or nonafluoromethoxybutane. The present invention further relates to ternary or quaternary azeotrope-like compositions consisting essentially of 1,1,1,3,3-pentafluorobutane and 1,1,1,2,3,4,4,5,5,5-decafluoropentane or nonafluoromethoxybutane, and additionally at least one of trans-1,2-dichloroethylene, n-propyl bromide, acetone, methanol, ethanol or isopropanol.

BACKGROUND

In recent years it has been pointed out that certain kinds of halogenated hydrocarbon compounds used in cleaning applications may adversely affect the stratospheric ozone layer when released into the atmosphere. Although this proposition has not yet been completely established, there is a movement toward the control of the use and the production of certain chlorofluorocarbon (CFC) and hydrochlorofluorocarbon (HCFC)-based cleaning compositions under an international agreement. Accordingly, there is a demand for the development of new compositions that have a lower ozone depletion potential than conventional CFC and HCFC-based cleaning compositions, while still achieving acceptable utility in cleaning applications.

In refrigeration and cleaning apparatus, compositions may be lost during operation through leaks in shaft seals, hose connections, soldered joints and broken lines. In addition, the working composition may be released to the atmosphere during maintenance procedures on equipment. If the composition is not a pure component or an azeotropic or azeotrope-like composition, the composition may change when leaked or discharged to the atmosphere from the equipment, which may cause the composition remaining in the equipment to become flammable or to exhibit unacceptable performance. Accordingly, it is desirable to use as a refrigerant or cleaning composition a single fluorinated hydrocarbon or an azeotropic or azeotrope-like composition which fractionates to a negilgible degree upon leak or boil off.

Hydrofluorocarbons (HFCs) have been proposed as replacements for CFCs and HCFCs in cleaning and drying compositions used by the electronics industry. However, many HFCs have limited solvency for electronics industry soils such as hydrocarbon or silicon oils and soldering flux residues. Accordingly, there is a need for HFC-based cleaning compositions which exhibit acceptable solubility for such electronics industry soils.

In applications where the potential of fire and fire's toxic byproducts are a concern, it is desirable for refrigerant and cleaning compositions to be nonflammable in both liquid and vapor phases, during operation and when charging fresh composition to a system or after composition has leaked from a system. Accordingly, it is preferred that compositions used to replace the conventional HCFC and CFC-based compositions are nonflammable.

It is also desireable that compositions offered to solve the aforementioned problems have a low global warming potential (GWP).

For the foregoing reasons, there is a need in the electronics industry, and industries supporting those requiring cleaning solutions, as well as the refrigeration industry, for compositions that solve the aforementioned problems.

SUMMARY

The compositions of the present invention solve the aforementioned multiple problems confronting the cleaning and refrigeration industries. The present compositions are: non-ozone depleting; low GWP; essentially non-fractioning azeotrope-like compositions; non-flammable; superior in refrigeration performance; and superior in cleaning performance and solubility for conventional-electronics industry soils (oils and fluxes). The present invention includes binary azeotrope-like compositions consisting essentially of 1,1,1,3,3-pentafluorobutane and 1,1,1,2,3,4,4,5,5,5-decafluoropentane or nonafluoromethoxybutane. The present invention further includes ternary or quaternary azeotrope-like compositions consisting essentially of 1,1,1,3,3-pentafluorobutane and 1,1,1,2,3,4,4,5,5,5-decafluoropentane or nonafluoromethoxybutane, and additionally trans-1,2-dichloroethylene (tDCE), n-propyl bromide (nPB), acetone, methanol, ethanol or isopropanol.

DETAILED DESCRIPTION

The azeotrope-like compositions of the present invention include 1,1,1,3,3-pentafluorobutane, and are selected from the group consisting of:

(i) compositions consisting essentially of from about 1 to about 99 weight percent 1,1,1,2,3,4,4,5,5,5-decafluoropentane and from about 1 to about 99 weight percent 1,1,1,3,3-pentafluorobutane, wherein said composition has a vapor pressure of from about 58.6 kPa to about 100.9 kPa at a temperature of about 40° C.;

(ii) compositions consisting essentially of from about 1 to about 95 weight percent 1,1,1,2,3,4,4,5,5,5-decafluoropentane, from about 1 to about 98 weight percent 1,1,1,3,3-pentafluorobutane and from about 1 to about 15 weight percent of methanol, wherein said composition has a vapor pressure of from about 72.9 kPa to about 112.2 kPa at a temperature of about 40° C.;

(iii) compositions consisting essentially of from about 1 to about 95 weight percent 1,1,1,2,3,4,4,5,5,5-decafluoropentane, from about 1 to about 98 weight percent 1,1,1,3,3-pentafluorobutane and from about 1 to about 15 weight percent ethanol, wherein said composition has a vapor pressure of from about 72.2 kPa to about 105.5 kPa at a temperature of about 40° C.;

(iv) compositions consisting essentially of from about 1 to about 95 weight percent 1,1,1,2,3,4,4,5,5,5-decafluoropentane, from about 1 to about 98 weight percent 1,1,1,3,3-pentafluorobutane and from about 1 to about 15 weight percent isopropanol, wherein said composition has a vapor pressure of from about 61.8 kPa to about 103.2 kPa at a temperature of about 40° C.;

(v) compositions consisting essentially of from about 1 to about 70 weight percent 1,1,1,2,3,4,4,5,5,5-decafluoropentane, from about 28 to about 98 weight percent 1,1,1,3,3-pentafluorobutane and from about 1 to about 10 weight percent acetone, wherein said composition has a vapor pressure of from about 73.8 kPa to about 100.3 kPa at a temperature of about 40° C.;

(vi) compositions consisting essentially of from about 1 to about 80 weight percent 1,1,1,2,3,4,4,5,5,5-decafluoropentane, from about 1 to about 98 weight percent 1,1,1,3,3-pentafluorobutane and from about 1 to about 66 weight percent trans-1,2-dichloroethylene, wherein said composition has a vapor pressure of from about 102.8 kPa to about 118.8 kPa at a temperature of about 40° C.;

(vii) compositions consisting essentially of from about 1 to about 60 weight percent 1,1,1,2,3,4,4,5,5,5-decafluoropentane, from about 10 to about 97 weight percent 1,1,1,3,3-pentafluorobutane, from about 1 to about 40 weight percent trans-1,2-dichloroethylene and from about 1 to about 10 weight percent of methanol, wherein said composition has a vapor pressure of from about 116.0 kPa to about 128.2 kPa at a temperature of about 40° C.;

(viii) compositions consisting essentially of from about 1 to about 60 weight percent 1,1,1,2,3,4,4,5,5,5-decafluoropentane, from about 10 to about 97 weight percent 1,1,1,3,3-pentafluorobutane, from about 1 to about 40 weight percent trans-1,2-dichloroethylene and from about 1 to about 10 weight percent ethanol, wherein said composition has a vapor pressure of from about 107.1 kPa to about 118.5 kPa at a temperature of about 40° C.;

(ix) compositions consisting essentially of from about 1 to about 60 weight percent 1,1,1,2,3,4,4,5,5,5-decafluoropentane, from about 10 to about 97 weight percent 1,1,1,3,3-pentafluorobutane, from about 1 to about 40 weight percent trans-1,2-dichloroethylene and from about 1 to about 10 weight percent isopropanol, wherein said composition has a vapor pressure of from about 104.6 kPa to about 114.9 kPa at a temperature of about 40° C.;

(x) compositions consisting essentially of from about 1 to about 50 weight percent 1,1,1,2,3,4,4,5,5,5-decafluoropentane, from about 30 to about 98 weight percent 1,1,1,3,3-pentafluorobutane and from about 1 to about 49 weight percent n-propyl bromide, wherein said composition has a vapor pressure of from about 70.9 kPa to about 106.5 kPa at a temperature of about 40° C.;

(xi) compositions consisting essentially of from about 1 to about 70 weight percent 1,1,1,2,3,4,4,5,5,5-decafluoropentane, from about 10 to about 97 weight percent 1,1,1,3,3-pentafluorobutane, from about 1 to about 35 weight percent n-propyl bromide, and from about 1 to about 10 weight percent of methanol, wherein said composition has a vapor pressure of from about 89.9 kPa to about 117.0 kPa at a temperature of about 40° C.;

(xii) compositions consisting essentially of from about 1 to about 70 weight percent 1,1,1,2,3,4,4,5,5,5-decafluoropentane, from about 10 to about 97 weight percent 1,1,1,3,3-pentafluorobutane, from about 1 to about 35 weight percent n-propyl bromide, and from about 1 to about 10 weight percent ethanol, wherein said composition has a vapor pressure of from about 85.8 kPa to about 108.3 kPa at a temperature of about 40° C.;

(xiii) compositions consisting essentially of from about 1 to about 70 weight percent 1,1,1,2,3,4,4,5,5,5-decafluoropentane, from about 10 to about 97 weight percent 1,1,1,3,3-pentafluorobutane, from about 1 to about 35 weight percent n-propyl bromide, and from about 1 to about 10 weight percent isopropanol, wherein said composition has a vapor pressure of from about 78.7 kPa to about 105.1 kPa at a temperature of about 40° C.;

(xiv) compositions consisting essentially of from about 1 to about 67 and from about 92 to about 99 weight percent nonafluoromethoxybutane and from about 33 to about 99 and from about 1 to about 8 weight percent 1,1,1,3,3-pentafluorobutane, wherein said composition has a vapor pressure of from about 50.1 kPa to about 100.9 kPa at a temperature of about 40° C.;

(xv) compositions consisting essentially of from about 1 to about 90 weight percent nonafluoromethoxybutane, from about 1 to about 98 weight percent 1,1,1,3,3-pentafluorobutane and from about 1 to about 15 weight percent of methanol, wherein said composition has a vapor pressure of from about 77.9 kPa to about 113.2 kPa at a temperature of about 40° C.;

(xvi) compositions consisting essentially of from about 1 to about 60 weight percent nonafluoromethoxybutane, from about 39 to about 98 weight percent 1,1,1,3,3-pentafluorobutane and from about 1 to about 10 weight percent ethanol, wherein said composition has a vapor pressure of from about 82.7 kPa to about 105.3 kPa at a temperature of about 40° C.;

(xvii) compositions consisting essentially of from about 1 to about 60 weight percent nonafluoromethoxybutane, from about 39 to about 98 weight percent 1,1,1,3,3-pentafluorobutane and from about 1 to about 10 weight percent isopropanol, wherein said composition has a vapor pressure of from about 82.1 kPa to about 103.1 kPa at a temperature of about 40° C.;

(xviii) compositions consisting essentially of from about 1 to about 98 weight percent nonafluoromethoxybutane, from about 1 to about 98 weight percent 1,1,1,3,3-pentafluorobutane and from about 1 to about 98 weight percent acetone, wherein said composition has a vapor pressure of from about 52.1 kPa to about 100.3 kPa at a temperature of about 40° C.;

(xix) compositions consisting essentially of from about 1 to about 75 weight percent nonafluoromethoxybutane, from about 1 to about 98 weight percent 1,1,1,3,3-pentafluorobutane and from about 1 to about 64 weight percent trans-1,2-dichloroethylene, wherein said composition has a vapor pressure of from about 93.4 kPa to about 118.7 kPa at a temperature of about 40° C.;

(xx) compositions consisting essentially of from about 1 to about 60 weight percent nonafluoromethoxybutane, from about 20 to about 97 weight percent 1,1,1,3,3-pentafluorobutane, from about 1 to about 35 weight percent trans-1,2-dichloroethylene and from about 1 to about 10 weight percent of methanol, wherein said composition has a vapor pressure of from about 113.1 kPa to about 127.8 kPa at a temperature of about 40° C.;

(xxi) compositions consisting essentially of from about 1 to about 50 weight percent nonafluoromethoxybutane, from about 20 to about 97 weight percent 1,1,1,3,3-pentafluorobutane, from about 1 to about 35 weight percent trans-1,2-dichloroethylene and from about 1 to about 10 weight percent ethanol, wherein said composition has a vapor pressure of from about 104.9 kPa to about 113.8 kPa at a temperature of about 40° C.;

(xxii) compositions consisting essentially of from about 1 to about 50 weight percent nonafluoromethoxybutane, from about 20 to about 97 weight percent 1,1,1,3,3-pentafluorobutane, from about 1 to about 35 weight percent trans-1,2-dichloroethylene and from about 1 to about 9 weight percent isopropanol, wherein said composition has a vapor pressure of from about 103.8 kPa to about 111.1 kPa at a temperature of about 40° C.;

(xxiii) compositions consisting essentially of from about 1 to about 50 weight percent nonafluoromethoxybutane, from about 30 to about 98 weight percent 1,1,1,3,3-pentafluorobutane and from about 1 to about 49 weight percent n-propyl bromide, wherein said composition has a vapor pressure of from about 90.7 kPa to about 106.6 kPa at a temperature of about 40° C.; and (xxiv) compositions consisting essentially of from about 1 to about 70 weight percent nonafluoromethoxybutane, from about 10 to about 97 weight percent 1,1,1,3,3-pentafluorobutane, from about 1 to about 35 weight percent n-propyl bromide and from about 1 to about 10 weight percent of methanol, wherein said composition has a vapor pressure of from about 93.4 kPa to about 118.0 kPa at a temperature of about 40° C., and wherein after 50 weight percent of said composition is evaporated or boiled off, the vapor pressure of the composition remaining has changed from the vapor pressure of said composition before evaporation or boil-off by 10 percent or less.

Preferably, the azeotrope-like compositions of the present invention are selected from the group consisting of:

(i) compositions consisting essentially of from about 10 to about 90 weight percent 1,1,1,2,3,4,4,5,5,5-decafluoropentane and from about 10 to about 90 weight percent 1,1,1,3,3-pentafluorobutane, wherein said composition has a vapor pressure of from about 65.9 kPa to about 98.9 kPa at a temperature of about 40° C.;

(ii) compositions consisting essentially of from about 10 to about 40 weight percent 1,1,1,2,3,4,4,5,5,5-decafluoropentane, from about 50 to about 89 weight percent 1,1,1,3,3-pentafluorobutane and from about 1 to about 10 weight percent of methanol, wherein said composition has a vapor pressure of from about 100.1 kPa to about 110.4 kPa at a temperature of about 40° C.;

(iii) compositions consisting essentially of from about 10 to about 40 weight percent 1,1,1,2,3,4,4,5,5,5-decafluoropentane, from about 50 to about 89 weight percent 1,1,1,3,3-pentafluorobutane, from about 1 to about 10 weight percent ethanol, wherein said composition has a vapor pressure of from about 96.9 kPa to about 103.8 kPa at a temperature of about 40° C.;

(iv) compositions consisting essentially of from about 10 to about 40 weight percent 1,1,1,2,3,4,4,5,5,5-decafluoropentane, from about 50 to about 89 weight percent 1,1,1,3,3-pentafluorobutane and from about 1 to about 10 weight percent isopropanol, wherein said composition has a vapor pressure of from about 92.5 kPa to about 101.1 kPa at a temperature of about 40° C.;

(v) compositions consisting essentially of from about 10 to about 40 weight percent 1,1,1,2,3,4,4,5,5,5-decafluoropentane, from about 50 to about 89 weight percent 1,1,1,3,3-pentafluorobutane and from about 1 to about 10 weight percent acetone, wherein said composition has a vapor pressure of from about 85.6 kPa to about 95.1 kPa at a temperature of about 40° C.;

(vi) compositions consisting essentially of from about 10 to about 50 weight percent 1,1,1,2,3,4,4,5,5,5-decafluoropentane, from about 20 to about 70 weight percent 1,1,1,3,3-pentafluorobutane and from about 10 to about 45 weight percent trans-1,2-dichloroethylene, wherein said composition has a vapor pressure of from about 114.2 kPa to about 118.0 kPa at a temperature of about 40° C.;

(vii) compositions consisting essentially of from about 10 to about 50 weight percent 1,1,1,2,3,4,4,5,5,5-decafluoropentane, from about 10 to about 50 weight percent 1,1,1,3,3-pentafluorobutane, from about 15 to about 45 weight percent trans-1,2-dichloroethylene and from about 1 to about 6 weight percent of methanol, wherein said composition has a vapor pressure of from about 116.0 kPa to about 128.2 kPa at a temperature of about 40° C.;

(viii) compositions consisting essentially of from about 10 to about 50 weight percent 1,1,1,2,3,4,4,5,5,5-decafluoropentane, from about 10 to about 50 weight percent 1,1,1,3,3-pentafluorobutane, from about 15 to about 45 weight percent trans-1,2-dichloroethylene and from about 1 to about 6 weight percent ethanol, wherein said composition has a vapor pressure of from about 114.1 kPa to about 119.3 kPa at a temperature of about 40° C.;

(ix) compositions consisting essentially of from about 10 to about 50 weight percent 1,1,1,2,3,4,4,5,5,5-decafluoropentane, from about 10 to about 50 weight percent 1,1,1,3,3-pentafluorobutane, from about 15 to about 45 weight percent trans-1,2-dichloroethylene and from about 1 to about 6 weight percent isopropanol, wherein said composition has a vapor pressure of from about 109.1 kPa to about 116.7 kPa at a temperature of about 40° C.;

(x) compositions consisting essentially of from about 10 to about 50 weight percent 1,1,1,2,3,4,4,5,5,5-decafluoropentane, from about 30 to about 70 weight percent 1,1,1,3,3-pentafluorobutane and from about 10 to about 40 weight percent n-propyl bromide, wherein said composition has a vapor pressure of from about 91.1 kPa to about 106.3 kPa at a temperature of about 40° C.;

(xi) compositions consisting essentially of from about 10 to about 50 weight percent 1,1,1,2,3,4,4,5,5,5-decafluoropentane, from about 20 to about 70 weight percent 1,1,1,3,3-pentafluorobutane, from about 12 to about 35 weight percent n-propyl bromide, and from about 1 to about 6 weight percent of methanol, wherein said composition has a vapor pressure of from about 98.8 kPa to about 110.8 kPa at a temperature of about 40° C.;

(xii) compositions consisting essentially of from about 10 to about 50 weight percent 1,1,1,2,3,4,4,5,5,5-decafluoropentane, from about 20 to about 70 weight percent 1,1,1,3,3-pentafluorobutane, from about 12 to about 35 weight percent n-propyl bromide, and from about 1 to about 6 weight percent ethanol, wherein said composition has a vapor pressure of from about 93.8 kPa to about 103.3 kPa at a temperature of about 40° C.;

(xiii) compositions consisting essentially of from about 10 to about 50 weight percent 1,1,1,2,3,4,4,5,5,5-decafluoropentane, from about 20 to about 70 weight percent 1,1,1,3,3-pentafluorobutane, from about 12 to about 35 weight percent n-propyl bromide, and from about 1 to about 6 weight percent isopropanol, wherein said composition has a vapor pressure of from about 89.6 kPa to about 99.1 kPa at a temperature of about 40° C.;

(xiv) compositions consisting essentially of from about 20 to about 60 weight percent nonafluoromethoxybutane and from about 40 to about 80 weight percent 1,1,1,3,3-pentafluorobutane, wherein said composition has a vapor pressure of from about 82.7 kPa to about 96.9 kPa at a temperature of about 40° C.;

(xv) compositions consisting essentially of from about 10 to about 40 weight percent nonafluoromethoxybutane, from about 50 to about 89 weight percent 1,1,1,3,3-pentafluorobutane and from about 1 to about 10 weight percent of methanol, wherein said composition has a vapor pressure of from about 107.0 kPa to about 113.2 kPa at a temperature of about 40° C.;

(xvi) compositions consisting essentially of from about 10 to about 40 weight percent nonafluoromethoxybutane, from about 48 to about 89 weight percent 1,1,1,3,3- pentafluorobutane and from about 1 to about 6 weight percent ethanol, wherein said composition has a vapor pressure of from about 92.0 kPa to about 102.2 kPa at a temperature of about 40° C.;

(xvii) compositions consisting essentially of from about 10 to about 40 weight percent nonafluoromethoxybutane, from about 48 to about 89 weight percent 1,1,1,3,3-pentafluorobutane and from about 1 to about 6 weight percent isopropanol, wherein said composition has a vapor pressure of from about 90.7 kPa to about 100.5 kPa at a temperature of about 40° C.;

(xviii) compositions consisting essentially of from about 10 to about 40 weight percent nonafluoromethoxybutane, from about 40 to about 80 weight percent 1,1,1,3,3-pentafluorobutane and from about 1 to about 10 weight percent acetone, wherein said composition has a vapor pressure of from about 88.0 kPa to about 96.3 kPa at a temperature of about 40° C.;

(xix) compositions consisting essentially of from about 10 to about 50 weight percent nonafluoromethoxybutane, from about 30 to about 70 weight percent 1,1,1,3,3-pentafluorobutane and from about 10 to about 40 weight percent trans-1,2-dichloroethylene, wherein said composition has a vapor pressure of from about 104.9 kPa to about 116.3 kPa at a temperature of about 40° C.;

(xx) compositions consisting essentially of from about 10 to about 50 weight percent nonafluoromethoxybutane, from about 20 to about 70 weight percent 1,1,1,3,3-pentafluorobutane, from about 15 to about 45 weight percent trans-1,2-dichloroethylene and from about 1 to about 6 weight percent of methanol, wherein said composition has a vapor pressure of from about 121.1 kPa to about 127.8 kPa at a temperature of about 40° C.;

(xxi) compositions consisting essentially of from about 10 to about 50 weight percent nonafluoromethoxybutane, from about 20 to about 70 weight percent 1,1,1,3,3-pentafluorobutane, from about 12 to about 45 weight percent trans-1,2-dichloroethylene and from about 1 to about 6 weight percent ethanol, wherein said composition has a vapor pressure of from about 104.9 kPa to about 114.8 kPa at a temperature of about 40° C.;

(xxii) compositions consisting essentially of from about 10 to about 50 weight percent nonafluoromethoxybutane, from about 20 to about 70 weight percent 1,1,1,3,3-pentafluorobutane, from about 12 to about 45 weight percent trans-1,2-dichloroethylene and from about 1 to about 6 weight percent isopropanol, wherein said composition has a vapor pressure of from about 103.8 kPa to about 113.6 kPa at a temperature of about 40° C.;

(xxiii) compositions consisting essentially of from about 10 to about 50 weight percent nonafluoromethoxybutane, from about 30 to about 70 weight percent 1,1,1,3,3-pentafluorobutane and from about 10 to about 40 weight percent n-propyl bromide, wherein said composition has a vapor pressure of from about 90.7 kPa to about 106.6 kPa at a temperature of about 40° C.; and (xxiv) compositions consisting essentially of from about 10 to about 50 weight percent nonafluoromethoxybutane, from about 20 to about 70 weight percent 1,1,1,3,3-pentafluorobutane, from about 12 to about 35 weight percent n-propyl bromide and from about 1 to about 6 weight percent of methanol, wherein said composition has a vapor pressure of from about 101.8 kPa to about 113.2 kPa at a temperature of about 40° C., and wherein after 50 weight percent of said composition is evaporated or boiled off, the vapor pressure of the composition remaining has changed from the vapor pressure of said composition before evaporation or boil-off by 10 percent or less.

As previously indicated, in refrigeration and cleaning apparatus, compositions may be lost during operation through leaks in shaft seals, hose connections, soldered joints and broken lines. In addition, the working composition may be released to the atmosphere during maintenance procedures on equipment. If the composition is not a pure component or an azeotropic or azeotrope-like composition, the composition may change when leaked or discharged to the atmosphere from the equipment, which may cause the composition remaining in the equipment to become flammable or to exhibit unacceptable performance. Accordingly, it is desirable to use as a refrigerant or cleaning composition a single fluorinated hydrocarbon or an azeotropic or azeotrope-like composition, such as the present invention, that fractionates to a negilgible degree upon leak or boil off.

By azeotrope-like composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, that is, the admixture distills/refluxes without substantial composition change. Another way to characterize an azeotrope-like composition is that the bubble point vapor pressure and the dew point vapor pressure of the composition at a particular temperature are substantially the same. Herein, a composition is azeotrope-like if, after 50 weight percent of the composition is removed such as by evaporation or boiling off, the difference in vapor pressure between the original composition and the composition remaining after 50 weight percent of the original composition has been removed by evaporation of boil off is less than 10 percent.

Herein, 1,1,1,3,3-pentafluorobutane may be referred to as HFC-365mfc, 1,1,1,2,3,4,4,5,5,5-decafluoropentane may be referred to as HFC-43-10mee, trans-1,2-dichloroethylene may be referred to as tDCE, and n-propylbromide may be referred to as nPB.

Nonafluoromethoxybutane ($C_4F_9OCH_3$) isomers of the present invention include 1,1,1,1,3,3-hexafluoro-2-methoxy-2-(trifluoromethyl)propane ($CH_3OC(CF_3)_3$), 1,1,1,2,2,3,3,4,4-nonafluoro-4-methoxybutane ($CH_3OCF_2CF_2CF_2CF_3$), 1,1,1,2,3,3-hexafluoro-2-(trifluoromethyl)-3-methoxypropane ($CH_3OCF_2CF(CF_3)_2$), and 1,1,1,2,3,3,4,4,4-nonafluoro-2-methoxybutane ($CH_3OCF(CF_3)CF_2CF_3$) with approximate isomer boiling points of 60° C. Other components of the compositions of the present invention include the following: HFC-43-10mee, normal boiling point 54° C.; HFC-365mfc, normal boiling point 40° C.; methanol, normal boiling point 65° C.; ethanol, normal boiling point 78° C.; isopropanol, normal boiling point 82° C.; n-propylbromide, normal boiling point 71° C.; trans-1,2-dichloroethylene, normal boiling point 48° C.; and acetone, normal boiling point 56° C.

The pure components forming the compositions of the present invention have the following vapor pressures at 40° C.:

| Component | Psia | kPa |
| --- | --- | --- |
| HFC-365mfc | 14.67 | 101.1 |
| HFC-43-10mee | 8.36 | 57.6 |
| $C_4F_9OCH_3$ | 7.07 | 48.7 |

-continued

| Component | Psia | kPa |
|---|---|---|
| tDCE | 11.27 | 77.7 |
| nPB | 4.18 | 28.8 |
| Methanol | 5.11 | 35.2 |
| Ethanol | 2.59 | 17.9 |
| Isopropanol | 2.00 | 13.8 |
| Acetone | 8.19 | 56.5 |

Substantially constant boiling, azeotrope-like compositions were surprisingly discovered by the present inventors and include the below compositions (in weight percent) at a temperature of 40° C. (in the below table, HFC-43-10mee is further abbreviated as 43-10mee and HFC-365mfc is further abbreviated as 365mfc):

| Composition | Azeotrope-like Range | Preferred Range |
|---|---|---|
| 43-10mee/365mfc | 1-99/1-99 | 10-90/10-90 |
| 43-10mee/365mfc/methanol | 1-95/1-98/1-15 | 10-40/50-89/1-10 |
| 43-10mee/365mfc/ethanol | 1-95/1-98/1-15 | 10-40/50-89/1-10 |
| 43-10mee/365mfc/isopropanol | 1-95/1-98/1-15 | 10-40/50-89/1-10 |
| 43-10mee/365mfc/acetone | 1-70/28-98/1-10 | 10-40/50-89/1-10 |
| 43-10mee/365mfc/tDCE | 1-80/1-98/1-66 | 10-50/20-70/10-45 |
| 43-10mee/365mfc/tDCE/methanol | 1-60/10-97/1-45/1-10 | 10-50/10-50/15-45/1-6 |
| 43-10mee/365mfc/tDCE/ethanol | 1-60/10-97/1-45/1-10 | 10-50/10-50/15-45/1-6 |
| 43-10mee/365mfc/tDCE/isopropanol | 1-60/10-97/1-45/1-10 | 10-50/10-50/15-45/1-6 |
| 43-10mee/365mfc/nPB | 1-50/30-98/1-49 | 10-50/30-70/10-40 |
| 43-10mee/365mfc/nPB/methanol | 1-70/10-97/1-35/1-10 | 10-50/20-70/12-35/1-6 |
| 43-10mee/365mfc/nPB/ethanol | 1-70/10-97/1-35/1-10 | 10-50/20-70/12-35/1-6 |
| 43-10mee/365mfc/nPB/isopropanol | 1-70/10-97/1-35/1-10 | 10-50/20-70/12-35/1-6 |
| $C_4F_9OCH_3$/365mfc | 1-67/33-99, 92-99/1-8 | 20-60/40-80 |
| $C_4F_9OCH_3$/365mfc/methanol | 1-90/1-98/1-15 | 10-40/50-89/1-10 |
| $C_4F_9OCH_3$/365mfc/ethanol | 1-60/39-98/1-10 | 10-40/48-89/1-6 |
| $C_4F_9OCH_3$/365mfc/isopropanol | 1-60/39-98/1-10 | 10-40/48-89/1-6 |
| $C_4F_9OCH_3$/365mfc/acetone | 1-98/1-98/1-98 | 10-40/40-80/1-10 |
| $C_4F_9OCH_3$/365mfc/tDCE | 1-75/1-98/1-64 | 10-50/30-70/10-40 |
| $C_4F_9OCH_3$/365mfc/tDCE/methanol | 1-60/20-97/1-50/1-10 | 10-50/20-70/15-45/1-6 |
| $C_4F_9OCH_3$/365mfc/tDCE/ethanol | 1-50/20-97/1-50/1-10 | 10-50/20-70/12-45/1-6 |
| $C_4F_9OCH_3$/365mfc/tDCE/isoprop | 1-50/20-97/1-50/1-9 | 10-50/20-70/12-45/1-6 |
| $C_4F_9OCH_3$/365mfc/nPB | 1-50/30-98/1-49 | 10-50/30-70/10-40 |
| $C_4F_9OCH_3$/365mfc/nPB/methanol | 1-70/10-97/1-35/1-10 | 10-50/20-70/12-35/1-6 |

By effective amount is meant the amount of each component of the inventive compositions which, when combined, results in the formation of an azeotrope-like composition. This definition includes the amounts of each component, which amounts may vary depending on the pressure applied to the composition so long as the azeotrope-like compositions continue to exist at the different pressures, but with possible different boiling points. Therefore, effective amount includes the amounts, such as may be expressed in weight percentages, of each component of the compositions of the instant invention that form an azeotrope-like compositions at temperatures or pressures other than as described herein. Therefore, effective amount includes the amounts of each component of the compositions of the instant invention which form azeotrope-like compositions at temperatures or pressures other than as described herein.

The azeotrope-like compositions of the present invention can be prepared by any convenient method including mixing or combining the desired amounts. A preferred method is to weigh the desired component amounts and thereafter combine them in an appropriate container.

The present compositions have low global warming potential. HFC-43-10mee has a 100 year GWP of 1300, whereas, HFC-365mfc has a 100 year GWP of 840. Though HFC-365mfc is flammable, mixtures of HFC-43-10mee and HFC-365mfc may be nonflammable and have a lower overall global warming impact than compositions comprising HFC-43-10mee as the only HFC component.

The present inventors discovered that replacement of HFC-43-10mee or $C_4F_9OCH_3$ in the presence of trans-dichloroethylene, n-propyl bromide or acetone with HFC-365mfc in compositions of the present invention, lowers global warming contribution and unexpectedly improves oil solubility.

Other components, such as aliphatic hydrocarbons having a boiling point of about 0 to 100° C., hydrofluorocarbon alkanes having a boiling point of about 0 to 100° C., hydrofluoropropanes having a boiling point of between about 0 to 100° C., hydrocarbon esters having a boiling point between about 0 to 100° C., hydrochlorofluorocarbons having a boiling point between about 0 to 100° C., hydrofluorocarbons having a boiling point of about 0 to 100° C., hydrochlorocarbons having a boiling point between about 0 to 100° C., chlorocarbons and perfluorinated compounds, may be added in small amounts to the azeotropic or azeotrope-like compositions described above without substantially changing the properties thereof, including the constant boiling behavior, of the compositions.

Additives known in the cleaning and refrigeration fields such as lubricants, corrosion inhibitors, surfactants, stabilizers, anti-foam agents, dyes and other appropriate materials may be added to, and used in the presence of, the present compositions of the invention for a variety of purposes, provided that such additives do not have an adverse influence on the present compositions for their intended application or change the basic and novel characteristics of the present azeotrope-like compositions as claimed. For instance, fluoroalkyl phosphate surfactants such as those disclosed by Dishart in U.S. Pat. No. 5,908,022 may be dissolved in the present compositions. The resultant composition may find utility in dewatering (displacement drying) processes carried out in the semiconductor industry during fabrication of integrated circuits.

Although the present specification is directed to use of the present azeotrope-like compositions as cleaning agents and compression refrigerants, the present compositions may also find utility as expansion agents for polyolefins and polyurethanes (polymer foam blowing agents), aerosol propellants, heat transfer media, gaseous dielectrics, power cycle working fluids, polymerization media, particulate removal fluids, carrier fluids and buffing abrasive agents.

EXAMPLES

Specific examples illustrating the invention are given below. Unless otherwise stated therein, all percentages are by weight. In the following examples, HFC-43-10mee may be further abbreviated as 43-10mee, and HFC-365mfc may be further abbreviated as 365mfc.

Example 1

Impact of Vapor Leakage on Vapor Pressure

A vessel is charged with an initial composition at a temperature of 40° C., and the vapor pressure of the composition is measured. The composition is allowed to leak from the vessel, while the temperature is held constant at 40° C., until 50 weight percent of the initial composition is removed, at which time the vapor pressure of the composition remaining in the vessel is measured. The results are summarized in Table 1 below.

TABLE 1

| Composition | 0 Wt % Evaporated Psia | 0 Wt % Evaporated kPa | 50 wt % Evaporated Psia | 50 wt % Evaporated kPa | % Change |
|---|---|---|---|---|---|
| 43-10mee/365mfc | | | | | |
| 1/99 | 14.64 | 100.9 | 14.63 | 100.9 | 0.1% |
| 10/90 | 14.34 | 98.9 | 14.24 | 98.2 | 0.7% |
| 20/80 | 13.97 | 96.3 | 13.78 | 95.0 | 1.4% |
| 30/70 | 13.57 | 93.6 | 13.27 | 91.5 | 2.2% |
| 40/60 | 13.12 | 90.5 | 12.71 | 87.6 | 3.1% |
| 50/50 | 12.60 | 86.9 | 12.09 | 83.4 | 4.0% |
| 60/40 | 12.02 | 82.9 | 11.42 | 78.7 | 5.0% |
| 70/30 | 11.34 | 78.2 | 10.68 | 73.6 | 5.8% |
| 80/20 | 10.53 | 72.6 | 9.90 | 68.3 | 6.0% |
| 90/10 | 9.56 | 65.9 | 9.11 | 62.8 | 4.7% |
| 99/1 | 8.50 | 58.6 | 8.43 | 58.1 | 0.8% |
| 43-10mee/365mfc/methanol | | | | | |
| 20/75/5 | 16.01 | 110.4 | 15.77 | 108.7 | 1.5% |
| 1/98/1 | 16.13 | 111.2 | 15.00 | 103.4 | 7.0% |
| 10/89/1 | 15.81 | 109.0 | 14.64 | 100.9 | 7.4% |
| 10/80/10 | 16.28 | 112.2 | 15.86 | 109.4 | 2.6% |
| 30/69/1 | 14.99 | 103.4 | 13.71 | 94.5 | 8.5% |
| 30/64/6 | 15.55 | 107.2 | 15.14 | 104.4 | 2.6% |
| 40/59/1 | 14.52 | 100.1 | 13.16 | 90.7 | 9.4% |
| 35/64/1 | 14.76 | 101.8 | 13.44 | 92.7 | 8.9% |
| 45/54/1 | 14.26 | 98.3 | 12.86 | 88.7 | 9.8% |
| 45/50/5 | 14.81 | 102.1 | 14.26 | 98.3 | 3.7% |
| 60/35/5 | 13.88 | 95.7 | 13.21 | 91.1 | 4.8% |
| 70/30/5 | 11.34 | 78.2 | 10.68 | 73.6 | 5.8% |
| 80/15/5 | 12.27 | 84.6 | 11.69 | 80.6 | 4.7% |
| 90/5/5 | 11.22 | 77.4 | 10.94 | 75.4 | 2.5% |
| 95/3/2 | 10.66 | 73.5 | 9.74 | 67.2 | 8.6% |
| 1/84/15 | 16.42 | 113.2 | 15.35 | 105.8 | 6.5% |
| 84/1/15 | 10.57 | 72.9 | 9.93 | 68.5 | 6.1% |
| 22/75/3 | 15.89 | 109.6 | 15.48 | 106.7 | 2.6% |
| 43-10mee/365mfc/ethanol | | | | | |
| 20/75/5 | 14.79 | 102.0 | 14.59 | 100.6 | 1.4% |
| 22/75/3 | 14.78 | 101.9 | 14.62 | 100.8 | 1.1% |
| 1/98/1 | 15.30 | 105.5 | 15.00 | 103.4 | 2.0% |
| 10/89/1 | 15.05 | 103.8 | 14.63 | 100.9 | 2.8% |
| 10/80/10 | 14.94 | 103.0 | 14.41 | 99.4 | 3.5% |

TABLE 1-continued

| Composition | 0 Wt % Evaporated Psia | 0 Wt % Evaporated kPa | 50 wt % Evaporated Psia | 50 wt % Evaporated kPa | % Change |
|---|---|---|---|---|---|
| 30/69/1 | 14.23 | 98.1 | 13.64 | 94.0 | 4.1% |
| 30/64/6 | 14.38 | 99.1 | 14.07 | 97.0 | 2.2% |
| 40/59/1 | 14.06 | 96.9 | 13.03 | 89.8 | 7.3% |
| 35/64/1 | 14.25 | 98.3 | 13.34 | 92.0 | 6.4% |
| 45/54/1 | 13.86 | 95.6 | 12.68 | 87.4 | 8.5% |
| 46/50/4 | 13.80 | 95.1 | 13.46 | 92.8 | 2.5% |
| 60/35/5 | 13.04 | 89.9 | 12.61 | 86.9 | 3.3% |
| 70/35/5 | 11.34 | 78.2 | 10.68 | 73.6 | 5.8% |
| 80/15/5 | 11.75 | 81.0 | 11.39 | 78.5 | 3.1% |
| 90/5/5 | 10.93 | 75.4 | 10.76 | 74.2 | 1.6% |
| 95/3/2 | 10.75 | 74.1 | 10.42 | 71.8 | 3.1% |
| 84/1/15 | 10.47 | 72.2 | 9.70 | 66.9 | 7.4% |
| 43-10mee/365mfc/isopropanol | | | | | |
| 20/75/5 | 14.26 | 98.3 | 13.95 | 96.2 | 2.2% |
| 22/75/3 | 14.25 | 98.3 | 14.01 | 96.6 | 1.7% |
| 1/98/1 | 14.97 | 103.2 | 14.88 | 102.6 | 0.6% |
| 10/89/1 | 14.67 | 101.1 | 14.49 | 99.9 | 1.2% |
| 10/80/10 | 14.45 | 99.6 | 13.92 | 96.0 | 3.7% |
| 30/69/1 | 13.88 | 95.7 | 13.49 | 93.0 | 2.8% |
| 30/64/6 | 13.76 | 94.9 | 13.27 | 91.5 | 3.6% |
| 40/59/1 | 13.42 | 92.5 | 12.92 | 89.1 | 3.7% |
| 34/64/1 | 13.65 | 94.1 | 13.22 | 91.1 | 3.2% |
| 45/54/1 | 13.16 | 90.7 | 12.62 | 87.0 | 4.1% |
| 45/50/5 | 13.06 | 90.0 | 12.47 | 86.0 | 4.5% |
| 60/30/5 | 12.14 | 83.7 | 11.46 | 79.0 | 5.6% |
| 70/30/5 | 11.34 | 78.2 | 10.68 | 73.6 | 5.8% |
| 80/15/5 | 10.58 | 72.9 | 10.04 | 69.2 | 5.1% |
| 90/5/5 | 9.59 | 66.1 | 9.35 | 64.5 | 2.5% |
| 95/3/2 | 9.32 | 64.3 | 9.07 | 62.5 | 2.7% |
| 84/1/15 | 8.97 | 61.8 | 8.63 | 59.5 | 3.8% |
| 43-10mee/365mfc/acetone | | | | | |
| 20/75/5 | 13.17 | 90.8 | 12.31 | 84.9 | 6.5% |
| 20/79/1 | 13.80 | 95.1 | 13.46 | 92.8 | 2.5% |
| 20/72/8 | 12.75 | 87.9 | 11.55 | 79.6 | 9.4% |
| 30/65/5 | 12.60 | 86.9 | 11.50 | 79.3 | 8.7% |
| 35/61/4 | 12.50 | 86.2 | 11.45 | 78.9 | 8.4% |
| 40/57/3 | 12.42 | 85.6 | 11.46 | 79.0 | 7.7% |
| 50/47/3 | 11.83 | 81.6 | 10.75 | 74.1 | 9.1% |
| 1/98/1 | 14.54 | 100.3 | 14.50 | 100.0 | 0.3% |
| 60/38/2 | 11.44 | 78.9 | 10.47 | 72.2 | 8.5% |
| 70/28/2 | 10.71 | 73.8 | 9.73 | 67.1 | 9.2% |
| 10/80/10 | 13.19 | 90.9 | 12.28 | 84.7 | 6.7% |
| 43-10mee/365mfc/tDCE | | | | | |
| 27/45/28 | 17.08 | 117.8 | 16.99 | 117.1 | 0.5% |
| 47/1/52 | 16.18 | 111.6 | 15.82 | 109.1 | 2.2% |
| 1/50/49 | 17.23 | 118.8 | 16.94 | 116.8 | 1.7% |
| 1/83/16 | 17.04 | 117.5 | 16.69 | 115.1 | 2.1% |
| 80/1/19 | 16.05 | 110.7 | 15.11 | 104.2 | 5.9% |
| 45/1/54 | 16.16 | 111.4 | 15.64 | 107.8 | 3.2% |
| 1/45/54 | 17.08 | 117.8 | 16.56 | 114.2 | 3.0% |
| 1/33/66 | 16.55 | 114.1 | 14.99 | 103.4 | 9.4% |
| 1/98/1 | 14.91 | 102.8 | 14.75 | 101.7 | 1.1% |
| 35/33/32 | 16.94 | 116.8 | 16.90 | 116.5 | 0.2% |
| 20/60/20 | 17.01 | 117.3 | 16.65 | 114.8 | 2.1% |
| 10/40/50 | 17.05 | 117.6 | 16.73 | 115.4 | 1.9% |
| 50/30/20 | 16.57 | 114.2 | 15.97 | 110.1 | 3.6% |
| 60/10/30 | 16.46 | 113.5 | 16.39 | 113.0 | 0.4% |
| 25/45/30 | 17.12 | 118.0 | 17.06 | 117.6 | 0.4% |
| 43-10mee/365mfc/tDCE/methanol | | | | | |
| 30/40/25/5 | 18.59 | 128.2 | 18.36 | 126.6 | 1.2% |
| 1/97/1/1 | 16.38 | 112.9 | 15.14 | 104.4 | 7.6% |
| 20/50/20/10 | 18.50 | 127.6 | 17.66 | 121.8 | 4.5% |
| 50/30/15/5 | 17.82 | 122.9 | 16.55 | 114.1 | 7.1% |
| 60/20/17/3 | 17.75 | 122.4 | 16.69 | 115.1 | 6.0% |
| 49/10/40/1 | 17.51 | 120.7 | 16.98 | 117.1 | 3.0% |
| 40/23/35/2 | 16.82 | 116.0 | 16.78 | 115.7 | 0.2% |
| 30/50/14/6 | 18.14 | 125.1 | 17.19 | 118.5 | 5.2% |
| 10/70/12/8 | 18.33 | 126.4 | 17.55 | 121.0 | 4.3% |
| 20/33/45/2 | 18.40 | 126.9 | 17.94 | 123.7 | 2.5% |
| 26/20/50/4 | 18.16 | 125.2 | 17.85 | 123.1 | 1.7% |

TABLE 1-continued

| Composition | 0 Wt % Evaporated | | 50 wt % Evaporated | | % Change |
|---|---|---|---|---|---|
| | Psia | kPa | Psia | kPa | |
| *43-10mee/365mfc/tDCE/ethanol* | | | | | |
| 30/40/25/5 | 17.19 | 118.5 | 16.97 | 117.0 | 1.3% |
| 1/97/1/1 | 15.53 | 107.1 | 15.14 | 104.4 | 2.5% |
| 20/50/20/10 | 16.93 | 116.7 | 16.09 | 110.9 | 5.0% |
| 50/30/15/5 | 16.55 | 114.1 | 15.61 | 107.6 | 5.7% |
| 60/20/17/3 | 16.68 | 115.0 | 15.95 | 110.0 | 4.4% |
| 49/10/40/1 | 16.86 | 116.2 | 16.75 | 115.5 | 0.7% |
| 40/23/35/2 | 17.17 | 118.4 | 17.14 | 118.2 | 0.2% |
| 30/50/14/6 | 16.72 | 115.3 | 15.95 | 110.0 | 4.6% |
| 10/70/12/8 | 16.77 | 115.6 | 16.03 | 110.5 | 4.4% |
| 20/33/45/2 | 17.30 | 119.3 | 17.07 | 117.7 | 1.3% |
| 26/20/50/4 | 16.96 | 116.9 | 16.28 | 112.2 | 4.0% |
| *43-10mee/365mfc/tDCE/isopropanol* | | | | | |
| 30/40/25/5 | 16.62 | 114.6 | 16.22 | 111.8 | 2.4% |
| 1/97/1/1 | 15.21 | 104.9 | 15.00 | 103.4 | 1.4% |
| 20/50/20/10 | 16.31 | 112.5 | 15.39 | 106.1 | 5.6% |
| 50/30/15/5 | 15.82 | 109.1 | 14.55 | 100.3 | 8.0% |
| 60/20/17/3 | 15.99 | 110.2 | 14.90 | 102.7 | 6.8% |
| 49/10/40/1 | 16.46 | 113.5 | 16.40 | 113.1 | 0.4% |
| 40/23/35/2 | 16.67 | 114.9 | 16.58 | 114.3 | 0.5% |
| 30/50/14/6 | 16.10 | 111.0 | 15.14 | 104.4 | 6.0% |
| 10/70/12/8 | 16.26 | 112.1 | 15.49 | 106.8 | 4.7% |
| 20/33/45/2 | 16.93 | 116.7 | 16.66 | 114.9 | 1.6% |
| 26/20/50/4 | 16.43 | 113.3 | 15.71 | 108.3 | 4.4% |
| *43-10mee/365mfc/nPB* | | | | | |
| 27/45/28 | 14.36 | 99.0 | 13.71 | 94.5 | 4.5% |
| 1/50/49 | 15.24 | 105.1 | 13.74 | 94.7 | 9.8% |
| 1/60/39 | 15.45 | 106.5 | 15.00 | 103.4 | 2.9% |
| 1/98/1 | 14.88 | 102.6 | 14.73 | 101.6 | 1.0% |
| 20/60/20 | 14.98 | 103.3 | 14.68 | 101.2 | 2.0% |
| 60/10/30 | 11.45 | 78.9 | 10.71 | 73.8 | 6.5% |
| 80/1/19 | 10.29 | 70.9 | 10.22 | 70.5 | 0.7% |
| 35/33/32 | 13.64 | 94.0 | 12.68 | 87.4 | 7.0% |
| 50/30/20 | 13.22 | 91.1 | 12.56 | 86.6 | 5.0% |
| 20/70/10 | 15.05 | 103.8 | 14.76 | 101.8 | 1.9% |
| 5/55/40 | 15.22 | 104.9 | 14.57 | 100.5 | 4.3% |
| 40/40/20 | 13.90 | 95.8 | 13.33 | 91.9 | 4.1% |
| 25/45/30 | 14.40 | 99.3 | 13.71 | 94.5 | 4.8% |
| 10/70/20 | 15.42 | 106.3 | 15.25 | 105.1 | 1.1% |
| *43-10mee/365mfc/nPB/methanol* | | | | | |
| 30/40/25/5 | 15.70 | 108.2 | 14.91 | 102.8 | 5.0% |
| 1/97/1/1 | 16.33 | 112.6 | 15.13 | 104.3 | 7.3% |
| 20/50/20/10 | 16.22 | 111.8 | 15.10 | 104.1 | 6.9% |
| 50/30/15/5 | 14.81 | 102.1 | 14.14 | 97.5 | 4.5% |
| 60/20/17/3 | 13.97 | 96.3 | 13.27 | 91.5 | 5.0% |
| 70/10/15/5 | 13.04 | 89.9 | 12.56 | 86.6 | 3.7% |
| 40/22/35/3 | 14.33 | 98.8 | 13.05 | 90.0 | 8.9% |
| 30/50/14/6 | 16.07 | 110.8 | 15.54 | 107.1 | 3.3% |
| 10/70/12/8 | 16.97 | 117.0 | 16.61 | 114.5 | 2.1% |
| *43-10mee/365mfc/nPB/ethanol* | | | | | |
| 30/40/25/5 | 14.69 | 101.3 | 13.98 | 96.4 | 4.8% |
| 1/97/1/1 | 15.50 | 106.9 | 15.12 | 104.2 | 2.5% |
| 20/50/20/10 | 15.06 | 103.8 | 13.83 | 95.4 | 8.2% |
| 50/30/15/5 | 13.94 | 96.1 | 13.43 | 92.6 | 3.7% |
| 60/20/17/3 | 13.31 | 91.8 | 12.85 | 88.6 | 3.5% |
| 70/10/15/5 | 12.45 | 85.8 | 12.11 | 83.5 | 2.7% |
| 40/23/35/2 | 13.61 | 93.8 | 12.52 | 86.3 | 8.0% |
| 30/50/14/6 | 14.98 | 103.3 | 14.52 | 100.1 | 3.1% |
| 10/70/12/8 | 15.71 | 108.3 | 15.22 | 104.9 | 3.1% |
| *43-10mee/365mfc/nPB/isopropanol* | | | | | |
| 30/40/25/5 | 14.10 | 97.2 | 13.17 | 90.8 | 6.6% |
| 1/97/1/1 | 15.18 | 104.7 | 14.99 | 103.4 | 1.3% |
| 20/50/20/10 | 14.49 | 99.9 | 13.24 | 91.3 | 8.6% |
| 50/30/15/5 | 13.16 | 90.7 | 12.38 | 85.4 | 5.9% |
| 60/20/17/3 | 12.49 | 86.1 | 11.84 | 81.6 | 5.2% |
| 70/10/15/5 | 11.42 | 78.7 | 10.88 | 75.0 | 4.7% |
| 40/23/35/2 | 13.00 | 89.6 | 11.75 | 81.0 | 9.6% |
| 30/50/14/6 | 14.38 | 99.1 | 13.70 | 94.5 | 4.7% |
| 10/70/12/8 | 15.25 | 105.1 | 14.69 | 101.3 | 3.7% |
| $C_4F_9OCH_3/365mfc$ | | | | | |
| 1/99 | 14.64 | 100.9 | 14.63 | 100.9 | 0.1% |
| 10/90 | 14.38 | 99.1 | 14.3 | 98.6 | 0.6% |
| 20/80 | 14.05 | 96.9 | 13.86 | 95.6 | 1.4% |
| 30/70 | 13.66 | 94.2 | 13.32 | 91.8 | 2.5% |
| 40/60 | 13.2 | 91.0 | 12.68 | 87.4 | 3.9% |
| 50/50 | 12.66 | 87.3 | 11.91 | 82.1 | 5.9% |
| 60/40 | 12 | 82.7 | 11.01 | 75.9 | 8.3% |
| 67/33 | 11.45 | 78.9 | 10.31 | 71.1 | 10.0% |
| 99/1 | 7.27 | 50.1 | 7.13 | 49.2 | 1.9% |
| 92/8 | 8.52 | 58.7 | 7.67 | 52.9 | 10.0% |
| $C_4F_9OCH_3/365mfc/methanol$ | | | | | |
| 20/75/5 | 16.29 | 112.3 | 16.16 | 111.4 | 0.8% |
| 22/75/3 | 16.20 | 111.7 | 15.87 | 109.4 | 2.0% |
| 1/98/1 | 16.15 | 111.4 | 15.01 | 103.5 | 7.1% |
| 10/89/1 | 15.97 | 110.1 | 14.66 | 101.1 | 8.2% |
| 10/80/10 | 16.42 | 113.2 | 16.14 | 111.3 | 1.7% |
| 30/68/2 | 15.86 | 109.4 | 14.72 | 101.5 | 7.2% |
| 30/64/6 | 15.94 | 109.9 | 15.69 | 108.2 | 1.6% |
| 40/58/2 | 15.52 | 107.0 | 14.10 | 97.2 | 9.1% |
| 60/35/5 | 14.57 | 100.5 | 13.97 | 96.3 | 4.1% |
| 80/15/5 | 13.00 | 89.6 | 12.34 | 85.1 | 5.1% |
| 90/5/5 | 11.87 | 81.8 | 11.49 | 79.2 | 3.2% |
| 84/1/15 | 11.30 | 77.9 | 11.11 | 76.6 | 1.7% |
| $C_4F_9OCH_3/365mfc/ethanol$ | | | | | |
| 20/75/5 | 14.41 | 99.4 | 13.80 | 95.1 | 4.2% |
| 22/75/3 | 14.36 | 99.0 | 13.89 | 95.8 | 3.3% |
| 1/98/1 | 15.27 | 105.3 | 15.00 | 103.4 | 1.8% |
| 10/89/1 | 14.83 | 102.2 | 14.58 | 100.5 | 1.7% |
| 10/80/10 | 14.73 | 101.6 | 13.81 | 95.2 | 6.2% |
| 30/68/2 | 13.86 | 95.6 | 13.40 | 92.4 | 3.3% |
| 30/64/6 | 13.79 | 95.1 | 12.70 | 87.6 | 7.9% |
| 40/58/2 | 13.35 | 92.0 | 12.56 | 86.6 | 5.9% |
| 50/48/2 | 12.70 | 87.6 | 11.64 | 80.3 | 8.3% |
| 60/39/1 | 11.99 | 82.7 | 10.84 | 74.7 | 9.6% |
| $C_4F_9OCH_3/365mfc/isopropanol$ | | | | | |
| 20/75/5 | 14.07 | 97.0 | 13.48 | 92.9 | 4.2% |
| 22/75/3 | 14.06 | 96.9 | 13.61 | 93.8 | 3.2% |
| 1/98/1 | 14.96 | 103.1 | 14.87 | 102.5 | 0.6% |
| 10/89/1 | 14.58 | 100.5 | 14.43 | 99.5 | 1.0% |
| 10/80/10 | 14.34 | 98.9 | 13.53 | 93.3 | 5.6% |
| 30/69/1 | 13.70 | 94.5 | 13.27 | 91.5 | 3.1% |
| 30/64/6 | 13.46 | 92.8 | 12.45 | 85.8 | 7.5% |
| 40/58/2 | 13.15 | 90.7 | 12.39 | 85.4 | 5.8% |
| 50/48/2 | 12.53 | 86.4 | 11.51 | 79.4 | 8.1% |
| 60/39/1 | 11.91 | 82.1 | 10.78 | 74.3 | 9.5% |
| $C_4F_9OCH_3/365mfc/acetone$ | | | | | |
| 20/75/5 | 13.59 | 93.7 | 13.34 | 92.0 | 1.8% |
| 20/79/1 | 13.96 | 96.3 | 13.76 | 94.9 | 1.4% |
| 20/70/10 | 13.14 | 90.6 | 12.80 | 88.3 | 2.6% |
| 30/55/15 | 12.33 | 85.0 | 11.91 | 82.1 | 3.4% |
| 40/40/20 | 11.53 | 79.5 | 11.12 | 76.7 | 3.6% |
| 40/20/40 | 10.27 | 70.8 | 9.97 | 68.7 | 2.9% |
| 20/40/40 | 10.86 | 74.9 | 10.28 | 70.9 | 5.3% |
| 10/30/60 | 9.96 | 68.7 | 9.28 | 64.0 | 6.8% |
| 30/10/60 | 9.60 | 66.2 | 9.20 | 63.4 | 4.2% |
| 10/60/30 | 11.82 | 81.5 | 11.17 | 77.0 | 5.5% |
| 30/60/10 | 12.76 | 88.0 | 12.37 | 85.3 | 3.1% |
| 60/30/10 | 11.28 | 77.8 | 10.70 | 73.8 | 5.1% |
| 60/10/30 | 10.04 | 69.2 | 9.91 | 68.3 | 1.3% |
| 80/10/10 | 9.84 | 67.8 | 9.27 | 63.9 | 5.8% |
| 10/80/10 | 13.46 | 92.8 | 13.18 | 90.9 | 2.1% |
| 10/10/80 | 9.04 | 62.3 | 8.55 | 59.0 | 5.4% |
| 98/1/1 | 7.55 | 52.1 | 7.29 | 50.3 | 3.4% |
| 1/98/1 | 14.55 | 100.3 | 14.53 | 100.2 | 0.1% |
| 1/1/98 | 8.28 | 57.1 | 8.21 | 56.6 | 0.8% |

TABLE 1-continued

|  | 0 Wt % Evaporated | | 50 wt % Evaporated | | |
| --- | --- | --- | --- | --- | --- |
| Composition | Psia | kPa | Psia | kPa | % Change |
| $C_4F_9OCH_3$/365mfc/tDCE | | | | | |
| 27/45/28 | 16.70 | 115.1 | 16.44 | 113.4 | 1.6% |
| 47/1/52 | 14.06 | 96.9 | 14.00 | 96.5 | 0.4% |
| 1/50/49 | 17.22 | 118.7 | 16.92 | 116.7 | 1.7% |
| 1/83/16 | 17.03 | 117.4 | 16.69 | 115.1 | 2.0% |
| 70/1/29 | 13.78 | 95.0 | 13.17 | 90.8 | 4.4% |
| 35/1/64 | 13.99 | 96.5 | 13.69 | 94.4 | 2.1% |
| 1/45/54 | 17.06 | 117.6 | 16.54 | 114.0 | 3.0% |
| 1/35/64 | 16.63 | 114.7 | 15.31 | 105.6 | 7.9% |
| 1/98/1 | 14.91 | 102.8 | 14.75 | 101.7 | 1.1% |
| 35/33/32 | 16.32 | 112.5 | 15.98 | 110.2 | 2.1% |
| 20/60/20 | 16.80 | 115.8 | 16.40 | 113.1 | 2.4% |
| 10/40/50 | 16.87 | 116.3 | 16.48 | 113.6 | 2.3% |
| 50/30/20 | 15.64 | 107.8 | 14.64 | 100.9 | 6.4% |
| 60/10/30 | 14.75 | 101.7 | 14.11 | 97.3 | 4.3% |
| 45/45/10 | 15.22 | 104.9 | 13.76 | 94.9 | 9.6% |
| 75/1/24 | 13.55 | 93.4 | 12.46 | 85.9 | 8.0% |
| 25/45/30 | 16.77 | 115.6 | 16.55 | 114.1 | 1.3% |
| $C_4F_9OCH_3$/365mfc/tDCE/methanol | | | | | |
| 30/40/25/5 | 18.53 | 127.8 | 18.29 | 126.1 | 1.3% |
| 1/97/1/1 | 16.4 | 113.1 | 15.14 | 104.4 | 7.7% |
| 20/50/20/10 | 18.52 | 127.7 | 17.88 | 123.3 | 3.5% |
| 50/30/15/5 | 17.57 | 121.1 | 16.6 | 114.5 | 5.5% |
| 60/20/17/3 | 17.28 | 119.1 | 16.13 | 111.2 | 6.7% |
| 40/23/35/2 | 17.92 | 123.6 | 16.87 | 116.3 | 5.9% |
| 30/50/14/6 | 18.15 | 125.1 | 17.44 | 120.2 | 3.9% |
| 10/70/12/8 | 18.38 | 126.7 | 17.74 | 122.3 | 3.5% |
| 20/33/45/2 | 18.36 | 126.6 | 17.57 | 121.1 | 4.3% |
| 26/20/50/4 | 18.26 | 125.9 | 17.85 | 123.1 | 2.2% |
| $C_4F_9OCH_3$/365mfc/tDCE/ethanol | | | | | |
| 30/40/25/5 | 16.26 | 112.1 | 15.28 | 105.4 | 6.0% |
| 1/97/1/1 | 15.51 | 106.9 | 15.14 | 104.4 | 2.4% |
| 20/50/21/9 | 16.38 | 112.9 | 14.93 | 102.9 | 8.9% |
| 40/23/35/2 | 15.76 | 108.7 | 15.15 | 104.5 | 3.9% |
| 50/20/27/3 | 15.21 | 104.9 | 14.11 | 97.3 | 7.2% |
| 30/50/15/5 | 16.03 | 110.5 | 14.65 | 101.0 | 8.6% |
| 10/70/12/8 | 16.51 | 113.8 | 15.45 | 106.5 | 6.4% |
| 20/33/45/2 | 16.65 | 114.8 | 16.17 | 111.5 | 2.9% |
| 26/20/50/4 | 15.73 | 108.5 | 14.83 | 102.2 | 5.7% |
| $C_4F_9OCH_3$/365mfc/tDCE/isopropanol | | | | | |
| 30/40/25/5 | 15.98 | 110.2 | 14.99 | 103.4 | 6.2% |
| 1/97/1/1 | 15.20 | 104.8 | 15.00 | 103.4 | 1.3% |
| 20/50/21/9 | 15.99 | 110.2 | 14.62 | 100.8 | 8.6% |
| 40/23/35/2 | 15.62 | 107.7 | 14.98 | 103.3 | 4.1% |
| 50/20/27/3 | 15.05 | 103.8 | 13.93 | 96.0 | 7.4% |
| 30/50/15/5 | 15.73 | 108.5 | 14.38 | 99.1 | 8.6% |
| 10/70/12/8 | 16.11 | 111.1 | 15.10 | 104.1 | 6.3% |
| 20/33/45/2 | 16.47 | 113.6 | 15.95 | 110.0 | 3.2% |
| 26/20/50/4 | 15.52 | 107.0 | 14.55 | 100.3 | 6.3% |
| $C_4F_9OCH_3$/365mfc/nPB | | | | | |
| 27/45/28 | 14.41 | 99.4 | 13.62 | 93.9 | 5.5% |
| 1/50/49 | 15.24 | 105.1 | 13.74 | 94.7 | 9.8% |
| 1/60/39 | 15.45 | 106.5 | 14.97 | 103.2 | 3.1% |
| 1/98/1 | 14.89 | 102.7 | 14.73 | 101.6 | 1.1% |
| 20/60/20 | 15.03 | 103.6 | 14.71 | 101.4 | 2.1% |
| 40/50/10 | 14.17 | 97.7 | 13.51 | 93.1 | 4.7% |
| 35/33/32 | 13.65 | 94.1 | 12.32 | 84.9 | 9.7% |
| 50/40/10 | 13.56 | 93.5 | 12.65 | 87.2 | 6.7% |
| 50/30/20 | 13.15 | 90.7 | 12.09 | 83.4 | 8.1% |
| 25/45/30 | 14.46 | 99.7 | 13.63 | 94.0 | 5.7% |
| 10/70/20 | 15.46 | 106.6 | 15.30 | 105.5 | 1.0% |
| $C_4F_9OCH_3$/365mfc/nPB/methanol | | | | | |
| 30/40/25/5 | 16.07 | 110.8 | 15.38 | 106.0 | 4.3% |
| 1/97/1/1 | 16.35 | 112.7 | 15.13 | 104.3 | 7.5% |
| 20/50/20/10 | 16.49 | 113.7 | 15.66 | 108.0 | 5.0% |
| 50/30/15/5 | 15.33 | 105.7 | 14.69 | 101.3 | 4.2% |
| 60/20/17/3 | 14.54 | 100.3 | 13.57 | 93.6 | 6.7% |
| 70/10/15/5 | 13.54 | 93.4 | 12.97 | 89.4 | 4.2% |
| 40/21/35/4 | 14.76 | 101.8 | 13.33 | 91.9 | 9.7% |
| 30/50/14/6 | 16.42 | 113.2 | 16.04 | 110.6 | 2.3% |
| 10/70/12/8 | 17.11 | 118.0 | 16.86 | 116.2 | 1.5% |

The results of this Example show that these compositions are azeotrope-like because when 50 wt. % of an original composition is removed, the vapor pressure of the remaining composition is within about 10% or less of the vapor pressure of the original composition, at a temperature of 40° C. Also, in some cases the pressure of a given composition is higher than the vapor pressure of any of the pure components in the composition.

Example 2

Distillation

A solution containing 30.0 wt % HFC-43-10mee and 70.0 wt % HFC-365mfc was prepared in a suitable container and mixed thoroughly. The solution was distilled in a five plate Oldershaw distillation column (7 cm diameter, 40 cm height) using a 10:1 reflux to take-off ratio. Head and pot temperatures were read directly to 1° C. The distillation was performed at a pressure of 760 mmHg. Distillate compositions were determined by gas chromatography. Results are summarized in Table 2.

TABLE 2

| Cuts | Temp (C.) Head | Wt % Distilled or Recovered | Weight Percentages in Cut | |
| --- | --- | --- | --- | --- |
| | | | 365mfc | 43-10mee |
| 1 | 40 | 18.2 | 89.1 | 10.9 |
| 2 | 40 | 27.3 | 88.2 | 11.8 |
| 3 | 40 | 36.3 | 87.0 | 13.0 |
| 4 | 40 | 45.5 | 85.0 | 15.0 |
| 5 | 40 | 54.7 | 81.6 | 18.4 |
| Heel | — | 91.5 | 18.5 | 81.5 |

Analysis of the above data indicates small differences in head temperatures and distillate compositions as the distillation progressed, indicating azeotrope-like behavior.

Example 3

Distillation

A solution containing 26.7 wt % HFC-43-10mee, 44.7 wt % HFC-365mfc and 28.6 wt % tDCE was prepared in a suitable container and mixed thoroughly. The solution was distilled in a five plate Oldershaw distillation column (7 cm diameter, 40 cm height) using a 10:1 reflux to take-off ratio. Head and pot temperatures were read directly to 1 C. The distillation was performed at a pressure of 757.53 mmHg. Distillate compositions were determined by gas chromatography. Results are summarized in Table 3.

TABLE 3

| Cuts | Temp (C.) Head | Wt % Distilled or Recovered | Weight Percentages in Cut | | |
|---|---|---|---|---|---|
| | | | 43-10mee | 365mfc | tDCE |
| 1 | 35 | 16.9 | 14.5 | 51.7 | 33.8 |
| 2 | 35 | 25.8 | 14.9 | 51.2 | 33.9 |
| 3 | 35 | 35.0 | 15.6 | 50.3 | 34.1 |
| 4 | 35 | 44.2 | 16.6 | 49.1 | 34.3 |
| 5 | 35 | 53.6 | 17.9 | 47.6 | 34.5 |
| Heel | — | 89.7 | 67.4 | 28.4 | 4.2 |

Analysis of the above data indicates small differences in head temperatures and distillate compositions as the distillation progressed, indicating azeotrope-like behavior.

Example 4

Oil Solubility

Compositions of the present invention were tested for room temperature solubility in mineral oil. Solubility was measured by weighing and placing an amount of oil in a suitable container, then slowly adding a composition of the present invention until the oil is completely dissolved. Results are shown in Table 4 below.

TABLE 4

| Composition | Wt % | % Solubility |
|---|---|---|
| 365mfc | 100% | <0.4 |
| 43-10mee/365mfc | 50/50 | <0.4 |
| $C_4F_9OCH_3$/365mfc | 50/50 | <0.4 |
| 365mfc/tDCE | 62/38 | 6.0 |
| 43-10mee/tDCE | 62/38 | 1.9 |
| 43-10mee/365mfc/tDCE | 31/31/38 | 4.4 |
| $C_4F_9OCH_3$/tDCE | 62/38 | 5.8 |
| $C_4F_9OCH_3$/365mfc/tDCE | 31/31/38 | 7.0 |
| 365mfc/nPB | 62/38 | 5.1 |
| 43-10mee/nPB | 62/38 | 1.8 |
| 43-10mee/365mfc/nPB | 31/31/38 | 4.6 |
| $C_4F_9OCH_3$/nPB | 62/38 | 5.4 |
| $C_4F_9OCH_3$/365mfc/nPB | 31/31/38 | 8.7 |

Though HFC-365mfc has relatively low solubility in mineral oil, it improves mineral oil solubility when displacing HFC-43-10mee or $C_4F_9OCH_3$ in a cleaning composition containing tDCE or n-propyl bromide (nPB). There is a synergistic effect between 365mfc and tDCE and with 365mfc and nPB which improves oil solubility.

Example 5

Oil Solubility

Solubility was measured by the method shown in Example 4 for pure compound and compositions of the present inventions. Results are given in Table 5 below.

TABLE 5

| Composition (wt %) | Wt % Solubility in DC-200 Silicone Oil | Wt % Solubility in Tapmatic Cutting Fluid |
|---|---|---|
| 43-10mee (100%) | Immiscible | Immiscible |
| $C_4F_9OCH_3$ (100%) | 0.9 | Immiscible |
| 365mfc | Immiscible | Immiscible |
| 43-10mee/tDCE 61%/39% | 3.5 | 9.6 |
| 43-10mee/365mfc/tDCE 33%/28%/39% | 17.0 | 18.6 |
| 43-10mee/nPB 80%/20% | 0.6 | 1.7 |
| 43-10mee/365mfc/nPB 20%/60%/20% | 0.7 | 19.8 |
| 43-10mee/acetone 97%/3% | Immiscible | Immiscible |
| 43-10mee/365mfc/acetone 50%/47%/3% | 0.6 | 0.5 |
| $C_4F_9OCH_3$/tDCE 68%/32% | 19.6 | 0.7 |
| $C_4F_9OCH_3$/365mfc/tCDE 35%/33%/32% | 27.1 | 25.1 |
| $C_4F_9OCH_3$/nPB 80%/20% | 11.6 | 0.6 |
| $C_4F_9OCH_3$/365mfc/nPB 20%/60%/20% | 12.0 | 25.7 |

Results show that addition of HFC-365mfc to the compositions above demonstrates an unexpected improvement in solubility even though 365mfc is immiscible with tapmatic cutting fluid and silicone DC-200 oil.

Example 6

Cleaning Performance

A suitable container was filled with compositions of the present invention shown in Table 4 and heated to the boiling point. Stainless steel nuts and bolts coated with various residues were suspended in the container for 10 seconds, then removed and observed. Results in Table 6 show residues are essentially completely removed.

Composition #1-25% 43-10mee/45% 365mfc/30% tDCE

Composition #2-30% 43-10mee/40% 365mfc/25% tDCE/5% Methanol

Composition #3-25% 43-10mee/45% 365mfc/30% nPB

Composition #4-30% 43-10mee/40% 365mfc/25% nPB/5% Methanol

Composition #5-25% $C_4F_9OCH_3$/45% 365mfc/30% tDCE

Composition #6-30% $C_4F_9OCH_3$/40% 365mfc/25% tDCE/5% Methanol

Composition #7-25% $C_4F_9OCH_3$/45% 365mfc/30% nPB

TABLE 6

| Composition | Boiling Point (° C.) | % REMOVED | | |
|---|---|---|---|---|
| | | DC-200 SILICONEOIL | TAPAMATIC CUTTING FLUID | MIL-5606G |
| Composition #1 | 35 | 100% | 100% | 98% |
| Composition #2 | 34 | 100% | 100% | 98% |
| Composition #3 | 44 | 100% | 100% | 98% |
| Composition #4 | 40 | 100% | 100% | 98% |
| Composition #5 | 36 | 100% | 100% | 98% |
| Composition #6 | 34 | 100% | 100% | 98% |
| Composition #7 | 43 | 100% | 100% | 98% |

Example 7

Cleaning Performance

A suitable container was filled with compositions of the present invention shown in Table 7 and heated to the boiling point. Stainless steel nuts and bolts coated with various residues were suspended in the container for 10 seconds, then removed and observed. Oil solubility was also measured. Results in Table 7 show residues are essentially completely removed.

Composition #1-33% 43-10mee/28% 365mfc/39% tDCE
Composition #2-10% 43-10mee/40% 365mfc/50% tDCE
Composition #3-45% 43-10mee/1% 365mfc/54% tDCE
Composition #4-20% 43-10mee/60% 365mfc/20% nPB
Composition #5-60% 43-10mee/10% 365mfc/30% nPB
Composition #6-40% 43-10mee/40% 365mfc/20% nPB
Composition #7-35% 43-10mee/61% 365mfc/4% Acetone
Composition #8-20% 43-10mee/72% 365mfc/8% Acetone
Composition #9-50% 43-10mee/47% 365mfc/3% Acetone
Composition #10-35% $C_4F_9OCH_3$/33% 365mfc/32% tDCE
Composition #11-10% $C_4F_9OCH_3$/40% 365mfc/50% tDCE
Composition #12-60% $C_4F_9OCH_3$/10% 365mfc/30% tDCE
Composition #13-20% $C_4F_9OCH_3$/60% 365mfc/20% nPB
Composition #14-50% $C_4F_9OCH_3$/30% 365mfc/20% nPB
Composition #15-1% $C_4F_9OCH_3$/50% 365mfc/49% nPB
Composition #16-20% $C_4F_9OCH_3$/70% 365mfc/10% Acetone
Composition #17-10% $C_4F_9OCH_3$/60% 365mfc/30% Acetone
Composition #18-30% $C_4F_9OCH_3$/10% 365mfc/60% Acetone
Composition #19-30% $C_4F_9OCH_3$/50% 365mfc/5% Methanol/15% nPB

TABLE 7

% Removed/Wt % Solubility

| Composition | DC-200 SILICONE OIL | TAPAMATIC CUTTING FLUID | Krytox ® | MIL-5606G |
|---|---|---|---|---|
| #1 - % Removed | 100% | 100% | 100% | 100% |
| % Solubility | 16.0% | 22.6% | 4.4% | 0.5% |
| #2 - % Removed | 100% | 100% | 100% | 100% |
| % Solubility | 22.2% | 41.5% | 2.9% | 21.2% |
| #3 - % Removed | 100% | 100% | 100% | 100% |
| % Solubility | 15.5% | 25.0% | 1.3% | 14.0% |
| #4 - % Removed | 100% | 100% | 100% | 100% |
| % Solubility | 1.4% | 12.6% | 5.6% | 0.4% |
| #5 - % Removed | 100% | 100% | 100% | 100% |
| % Solubility | 1.0% | 11.0% | 17.7% | 1.7% |
| #6 - % Removed | 100% | 100% | 100% | 100% |
| % Solubility | 0.8% | 2.7% | 29.0% | 0.5% |
| #7 - % Removed | 90% | 100% | 100% | 80% |
| % Solubility | 1.5% | 1.4% | 14.0% | Immiscible |
| #8 - % Removed | 60% | 100% | 100% | 90% |
| % Solubility | 1.1% | 2.6% | 1.9% | 0.9% |
| #9 - % Removed | 90% | 100% | 100% | 80% |
| % Solubility | 0.2% | 1.0% | 32.3% | Immiscible |
| #10 - % Removed | 100% | 100% | 100% | 100% |
| % Solubility | 12.9% | 25.2% | 21.8% | 0.2% |
| #11 - % Removed | 100% | 100% | 100% | 100% |
| % Solubility | 17.9% | 14.4% | 2.0% | 21.0% |
| #12 - % Removed | 100% | 100% | 100% | 100% |
| % Solubility | 15.1% | 1.6% | 22.7% | 0.3% |
| #13 - % Removed | 100% | 100% | 100% | 100% |
| % Solubility | 12.7% | 25.8% | 4.6% | 0.3% |
| #14 - % Removed | 100% | 100% | 100% | 100% |
| % Solubility | 9.6% | 19.4% | 32.8% | 0.4% |
| #15 - % Removed | 100% | 100% | 100% | 100% |
| % Solubility | 20.5% | 21.4% | Immiscible | 9.7% |
| #16 - % Removed | 90% | 100% | 100% | 80% |
| % Solubility | 1.4% | 1.9% | 19.6% | Immiscible |
| #17 - % Removed | 90% | 100% | 100% | 80% |
| % Solubility | 0.6% | 43.6% | Immiscible | 0.3% |
| #18 - % Removed | 95% | 100% | 100% | 85% |
| % Solubility | 23.1% | 39.2% | Immiscible | 0.4% |
| #19 - % Removed | 100% | 100% | 100% | 95% |
| % Solubility | 8.4% | 26.9% | 6.9% | 0.4% |

Krytox ® is a trademark of the DuPont Company

Example 8

Defluxing

Several single sided circuit boards were coated with Alpha 611F RMA rosin flux, then activated by heating to 165° C. for 2 minutes. The boards were defluxed by rinsing at room temperature with the compositions shown in Table 8. Results show significant residue removal using compositions of the present invention.

TABLE 8

| Composition | % Flux Removal |
|---|---|
| 30% 43-10mee/40% 365mfc/25% tDCE/5% Methanol | 99 |
| 30% 43-10mee/40% 365mfc/25% nPB/5% Methanol | 95 |
| 30% $C_4F_9OCH_3$/40% 365mfc/25% tDCE/5% Methanol | 100 |
| 30% $C_4F_9OCH_3$/40% 365mfc/25% tDCE/5% Isopropanol | 100 |

Example 9

Flammability Testing

Compositions of the present invention were tested for flammability by tag open cup method per ASTM 1310. No tag open cup flash points were observed for the compositions in Table 9 below, for the temperature ranges shown.

TABLE 9

| Composition | Weight Percent | Temp Range (C.) |
|---|---|---|
| 43-10mee/365mfc/tDCE | 25/45/30 | 0-36 |
| 43-10mee/365mfc/tDCE/ethanol | 30/40/25/5 | 0-36 |
| 43-10mee/365mfc/nPB | 25/45/30 | 0-35 |
| 43-10mee/365mfc/tDCE/isopropanol | 30/40/25/5 | 0-37 |
| $C_4F_9OCH_3$/365mfc/tDCE | 25/45/30 | 0-36 |
| $C_4F_9OCH_3$/365mfc/nPB | 25/45/30 | 0-44 |

Example 10

Flammability Testing

Compositions of the present invention were tested for flammability by tag closed cup method per ASTM D-56-93. No tag closed cup flash points were observed inside the cup for the compositions in Table 10 below, for the temperature ranges shown.

TABLE 10

| Composition | Weight Percent | Temp Range (C.) |
|---|---|---|
| 43-10mee/365mfc/ethanol | 60/15/5 | −10 to 38 |
| 43-10mee/365mfc/tDCE | 33/28/39 | −10 to 38 |
| 43-10mee/365mfc/tDCE | 45/1/54 | −10 to 38 |
| 43-10mee/365mfc/nPB | 20/60/20 | −10 to 38 |
| 43-10mee/365mfc/acetone | 70/28/2 | −10 to 38 |
| $C_4F_9OCH_3$/365mfc/ethanol | 60/35/5 | −10 to 38 |
| $C_4F_9OCH_3$/365mfc/isopropanol | 48/50/2 | −10 to 38 |
| $C_4F_9OCH_3$/365mfc/tDCE | 35/33/32 | −10 to 38 |
| $C_4F_9OCH_3$/365mfc/nPB | 20/60/20 | −10 to 38 |
| $C_4F_9OCH_3$/365mfc/acetone | 80/10/10 | −10 to 38 |
| 43-10mee/365mfc/tDCE/methanol | 40/23/35/2 | −10 to 38 |
| 43-10mee/365mfc/nPB/methanol | 60/20/17/3 | −10 to 38 |
| $C_4F_9OCH_3$/365mfc/nPB/isopropanol | 60/20/17/3 | −10 to 38 |
| $C_4F_9OCH_3$/365mfc/nPB/methanol | 50/30/15/5 | −10 to 38 |

Example 11

Global Warming

Replacing an amount of HFC-43-10mee in cleaning mixtures with HFC-365mfc reduces the global warming of the mixture as shown in Table 11. Pure component global warming data are taken from Scientific Assessment of Ozone Depletion, 1998 by the World Meterological Organization Global Ozone Research and Monitoring Project (Report No. 44, Geneva, 1999). Mixture GWPs are based on a weighted sum of individual component GWPs.

TABLE 11

| | 100 Yr GWP |
|---|---|
| HFC-4310mee | 1700 |
| HFC-365mfc | 910 |
| HFC-4310mee/HFC-365mfc wt % | |
| 90/10 | 1621 |
| 80/20 | 1542 |
| 60/40 | 1384 |
| 40/60 | 1226 |
| 20/80 | 1068 |
| 10/90 | 989 |

Example 12

Refrigerant Performance

Table 12 below shows the performance of compositions of the present invention as refrigerants. The data are based on the following conditions:

| Evaporator Temperature | 40.0 F. (4.4 C.) |
|---|---|
| Condenser Temperature | 110.0 F. (43.3 C.) |
| Subcooled | 10.0 F. (5.6 C.) |
| Return Gas Temperature | 75.0 F. (23.9 C.) |
| Compressor Efficiency | 70% |

The refrigeration capacity is based on a compressor with a fixed displacement of 3.5 cubic feet per minute and 70% volumetric efficiency. Capacity is intended to mean the change in enthalpy of the refrigerant in the evaporator per pound of refrigerant circulated. i.e. the heat removed by the refrigerant in the evaporator per time. Coefficient of Performance (COP) is intended to mean the ratio of capacity to compressor work. It is a measure of refrigerant energy efficiency.

TABLE 12

| Comp Wt % | Evap Psia | Cond Psia | Comp. Disch F | Glide Cond/Evap | COP | Cap (Btu/min) |
|---|---|---|---|---|---|---|
| CFC-113 | 2.7 | 12.8 | 156.3 | 0/0 | 4.18 | 14.8 |
| 43-10mee/365mfc | | | | | | |
| 5/95 | 3.6 | 16.1 | 145.9 | 0.1/0.2 | 4.09 | 21.1 |
| 30/70 | 3.3 | 15.3 | 142.9 | 1.1/1.5 | 4.07 | 19.6 |
| 95/5 | 2.1 | 10.9 | 133.7 | 1.1/1.3 | 3.96 | 13.0 |
| $C_4F_9OCH_3$/365mfc | | | | | | |
| 5/95 | 3.5 | 16.0 | 145.8 | 0.5/0.7 | 4.10 | 20.9 |
| 30/70 | 3.0 | 14.3 | 142.9 | 3.2/3.8 | 4.08 | 18.3 |
| 95/5 | 1.6 | 8.8 | 132.2 | 1.9/2.1 | 3.97 | 10.3 |

Results of this example show addition of 365mfc to 43-10mee or $C_4F_9OCH_3$ significantly improves capacity while providing lower compressor discharge temperatures and comparable pressures to CFC-113. Fractionation or glide in the condenser and evaporator also demonstrate azeotrope-like behavior.

What is claimed is:

1. An azeotrope-like 1,1,1,3,3-pentafluorobutane-containing composition, wherein said composition is selected from the group consisting of:
(i) compositions consisting essentially of from about 1 to about 60 weight percent 1,1,1,2,3,4,4,5,5,5-decafluoropentane, from about 10 to about 97 weight percent 1,1,1,3,3-pentafluorobutane, from about 41 to about 50 weight percent trans-1,2-dichloroethylene and from about 1 to about 10 weight percent ethanol, wherein said composition has a vapor pressure of from about 116.2 kPa to about 119.3 kPa at a temperature of about 40° C.;
(ii) compositions consisting essentially of from about 1 to about 50 weight percent nonafluoromethoxybutane, from about 20 to about 97 weight percent 1,1,1,3,3-pentafluorobutane, from about 36 to about 50 weight percent trans-1,2-dichloroethylene and from about 1 to about 9 weight percent isopropanol, wherein said composition has a vapor pressure of from about 107.0 kPa to about 113.6 kPa at a temperature of about 40° C.;
and wherein after 50 weight percent of said composition has evaporated the vapor pressure of the remaining composition has changed by about 10 percent or less.

2. A process for cleaning a surface comprising: contacting the surface with a composition of claim 1, and recovering the cleaned surface from the composition.

3. A process for producing refrigeration, comprising condensing a composition of claim 1, and thereafter evaporating said composition in the vicinity of a body to be cooled.

4. A process for producing heat, comprising condensing a composition of claim 1, in the vicinity of a body to be heated, and thereafter evaporating said composition.

* * * * *